Figure 1:
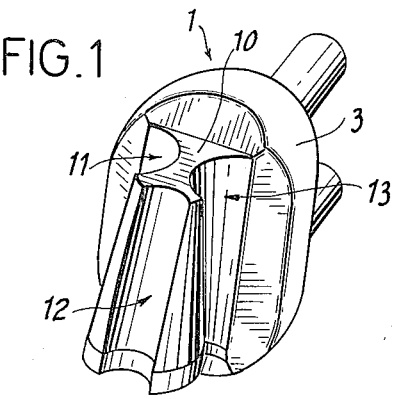

United States Patent [19]

Hader

[11] Patent Number: 4,475,891
[45] Date of Patent: Oct. 9, 1984

[54] DENTAL ATTACHMENT FOR FIXING DENTAL PROSTHESES

[76] Inventor: Helmut Hader, Les Allées 25, CH - 2300 La Chaux-de-Fonds, Switzerland

[21] Appl. No.: 471,674

[22] Filed: Mar. 3, 1983

[30] Foreign Application Priority Data

Mar. 31, 1982 [CH] Switzerland .................. 1977/82

[51] Int. Cl.³ .............................................. A61C 13/22
[52] U.S. Cl. .................................... 433/181; 433/191
[58] Field of Search ............... 433/181, 180, 192, 193, 433/182

[56] References Cited

U.S. PATENT DOCUMENTS

| 1,299,067 | 4/1919 | Underwood | 433/181 |
| 1,471,754 | 10/1923 | Rosenblum | 433/181 |
| 2,705,366 | 4/1955 | Van Dyk | 433/182 |
| 4,380,436 | 4/1983 | Kipp | 433/182 |

FOREIGN PATENT DOCUMENTS 619856 10/1980 Switzerland .................. 433/191

Primary Examiner—John J. Wilson
Attorney, Agent, or Firm—Young & Thompson

[57] ABSTRACT

A dental attachment for fixing a dental prosthesis to healthy teeth comprising a male portion 1 which is rigidly fixed to a living tooth and a female portion 2 which is fixed to the dental prosthesis, the male portion 1 comprising two pins 8 which are intended to be engaged and sealed by one of their ends in holes in a living tooth, the other end of the pins 8 having a heel portion 9 which is retained in a recess 5 provided in a male connecting member by means of a plate 6 having a T-shaped slot 7 through which the pins 8 extend, the thickness of a head portion 9 of the pins 8 being less than the depth of the recess 5, the male portion 1 also having a coupling portion 10 comprising three frustoconical drillings 11, 12, 13 having their axes parallel, the drillings 11, 12, 13 flaring outwardly upwardly and being disposed in a triangular configuration.

2 Claims, 8 Drawing Figures

DENTAL ATTACHMENT FOR FIXING DENTAL PROSTHESES

The present invention relates to an attachment for fixing dental prostheses.

The arrangements used hitherto for fixing dental prostheses require crowns to be fitted on to the healthy teeth on each side of the gap to be filled, to permit bridges and even partial dentures to be fixed on to the crowns. That procedure involves cutting healthy teeth which serve to carry the dental prostheses, thus making them much more vulnerable to infection and decay. It will be appreciated that that is not desirable, and systems have been developed, such as that described in Swiss Pat. No. 619 856, which use anchoring members comprising two teat elements which are intended to be fixed in a healthy tooth and which serve to carry a screwthread rod on to which are screwed studs which serve for fixing the prosthesis.

That arrangement is not satisfactory because it is necessary to drill two strictly parallel cavities to receive the teat elements, and that cannot be achieved under pratical conditions. In fact, this arrangement also involves the necessity of forming substantial openings in the healthy teeth serving to carry the anchoring means, in order to be able to secure them in the required position. In addition, the presence of the irremovable screwthreaded rods causes problems for the user, particularly when fixing removable units.

According to the present invention there is provided a dental attachment for fixing dental prostheses to healthy teeth, comprising a male portion which can be rigidly fixed to a healthy tooth and a female portion which is fixed to the dental prosthesis, the male portion comprising two pins which are intended to be secured by one of their ends in a healthy tooth, the other end of each of the pins, having a head portion which is retained in an opening provided in the male portion by means of a plate having a T-shaped slot through which the pins extend, the thickness of the head portions of the pins being less than the depth of the opening.

Figure 4:
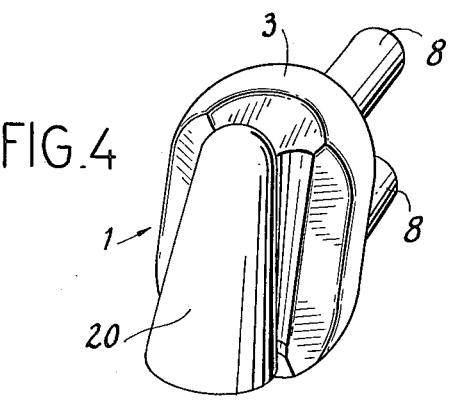
Figure 6:
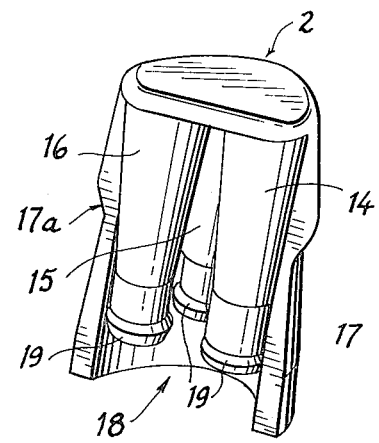
Figure 3:
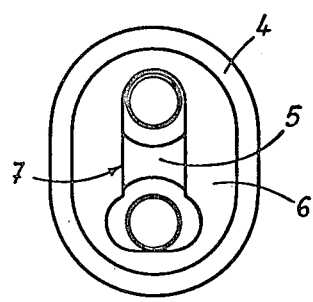
Figure 2:
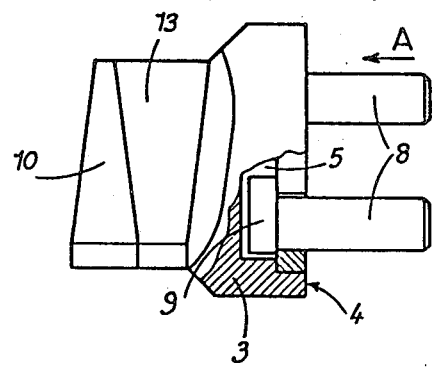
Figure 5:
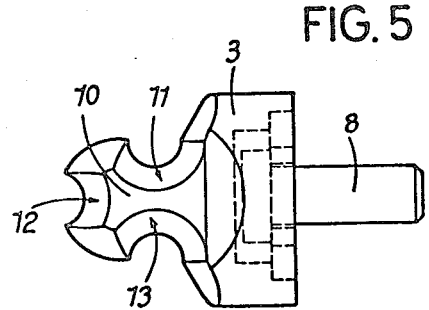
Figure 7:
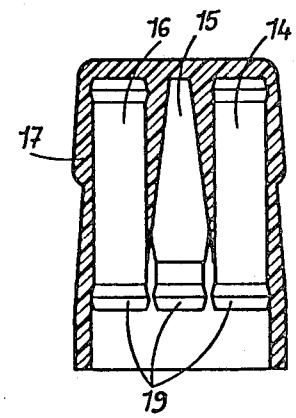
Figure 8:
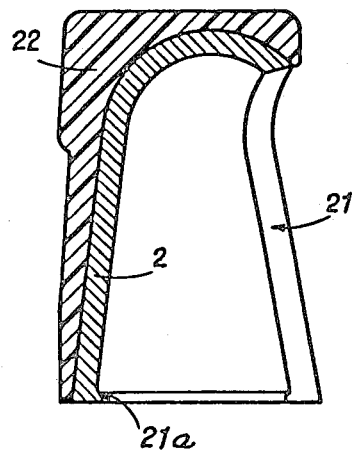

Two embodiments of the invention will now be described, by way of examples, with reference to the accompanying drawings, in which:

FIG. 1 is a perspective view of a male portion a first embodiment of an attachment according to the present invention, FIG. 2 is a partly sectional side view of the male portion illustrated in FIG. 1, FIG. 3 is a view taken in the direction of arrow A of the male portion illustrated in FIG. 2, FIG. 4 is a perspective view of a second embodiment of the male portion of an attachment according to the present invention, FIG. 5 is a plan view of the male portion illustrated in FIG. 2, FIG. 6 is a perspective view of a female portion of an attachment for co-operating with the male portion shown in FIGS. 1 to 3, FIG. 7 is a cross-sectional view of the female portion illustrated in FIG. 6, FIG. 8 is a cross-sectional view of a female portion for co-operating with the male portion illustrated in FIGS. 4 and 5.

The attachment illustrated in the drawings comprises a male portion 1 which is intended to be fixed in a healthy tooth, and a female portion 2 which is intended to be incorporated in or connected to a dental prosthesis.

In the first embodiment illustrated in FIGS. 1 to 3, 6 and 7, the male portion 1 comprises a body 3 having a flat rear face 4 in which a recess 5 is provided. The recess 5 is closed by a plate 6 provided with a T-shaped slot 7. The male portion further comprises two pegs or pins 8 which extend through the slot 7 and which each have a head or shoulder portion 9 which is trapped in the recess 5 in the body by the plate 6, the dimensions of the head or shoulder 4 being such that it does not pass through the slot 7. The thickness of the head portion 9 is less than the depth of the recess 5 so that the pins 8 can be displaced easily in the T-shaped slot 7 and may also assume substantially inclined positions both relative to each other and with respect to a line perpendicular to the face 4 of the body 3 of the male portion 1.

By virtue of this arrangement, the dentist can drill two small recesses, the dimensions of which correspond to those of the pins 8, in a healthy tooth, for receiving the pins 8. The recesses drilled in the tooth may be small in size and do not necessarily have to be parallel to each other nor spaced at a predetermined distance. In fact, as the pins 8 are movable with a translatory movement and with an angular movement, they can be easily fitted into the two drillings and then sealed therein. The opening 5 is also filled with a sealing material when the body 3 is correctly oriented to permit the prosthesis to be fixed in position.

The male portion 1 also comprises a coupling portion 10 having three conical millings or drillings 11, 12, 13 with their axes parallel. The conical drillings 11, 12, 13 each flare outwardly towards the upper face of the male portion 1.

The coupling portion 10 is intended to co-operate with a female portion 2 of the attachment, as illustrated in FIGS. 6 and 7 which comprises three pins 14, 15 and 16 mounted in a mass of plastics material 17 having an aperture 18.

The pins 14, 15 and 16 are also conical and flare outwardly in an upward direction, and at their lower end carry a retaining lip or lock portion 19.

The female portion 2 is intended to be incorporated in a dental prosthesis. That may be effected for example by providing, in the dental prosthesis, a cavity or opening which corresponds to the form of the mass of plastics material 17 of the female portion 2. The female portion 2 is then fastened in the manner of a press-stud in the opening in the dental prosthesis. It is retained in position by a shoulder 17a co-operating with the walls of the opening formed in the dental prosthesis.

To fix the dental prosthesis, it is sufficient to engage the pins 14, 15 and 16 in the drillings 11, 12 and 13, which is extremely simple because of the conical configuration of the pins 14, 15 and 16 and the drillings 11, 12, 13. By pushing the pins 14, 15, 16 right home into the drillings 11, 12, 13, the retaining lip portion 19 is moved into a position under the coupling portion 10 and holds the female and male portions 1 and 2 in the coupled position.

This attachment is particularly attractive for the following reasons:

1. Interference with the healthy teeth serving as a carrier is minimised, as the drillings may be small and the positions thereof are not critical, as also is the case with their orientation.

2. The dental prosthesis may be removably fixed in place.

3. The alignment of the two or more male portions serving to fix a prosthesis and likewise in regard to the female portions, is not a critical consideration, by virtue of the tapered configuration of the drillings 11, 12 and 13 and the pins 14, 15 and 16, as well as the elasticity of the mass of plastics material 17, which permit the portions automatically to assume their proper positions when the prosthesis is set in place.

4. As it can be manufactured on a mass-production basis, the cost price thereof can be kept low.

The second embodiment of the dental attachment illustrated in FIGS. 4 and 8 also comprises a male portion 1 and a female portion 2.

The male portion 1 comprises a body 3 and pegs or pins 8, in the same manner as the first embodiment. Only the portion forming the coupling means is different in shape. The coupling portion 20 is in the general shape of a cone pivot, the upper end of which is rounded, the side flaring outwardly downwardly.

The corresponding female portion 2 is formed by a conical cap member shown in FIG. 8, the internal form of which corresponds to the external form of the conical portion 20, and which has an aperture 21. The female portion 2 can thus be fitted on to the conical portion 20 once the latter is secured in the mouth, as has been described hereinbefore, by means of the pins 8.

The female portion 2 has a lower catch or lip portion 21a which co-operates with the lower edge of the conical portion 20 to lock the female portion on the portion 20 in the engaged position of use.

The female portion 2 may be made of a slightly elastic material such as a plastics material.

The female portion 2 is incorporated in the dental prosthesis 22 by any known means.

This second embodiment of the dental attachment enjoys the same advantages as those set forth above.

I claim:

1. A dental attachment for fixing dental prosthesis to healthy teeth, comprising a male portion which can be rigidly fixed to a healthy tooth and a female portion which is fixed to the dental prosthesis, the male portion comprising two pins which are adapted to be secured by one of their ends in a healthy tooth, the other end of each of said pins having a head portion which is retained in an opening provided in the male portion by means of a plate having a T-shaped slot through which the pins extend, the thickness of the head portions of the pins being less than the depth of the opening, the male portion having a coupling portion having three frustoconical drillings with their axes parallel, the drillings flaring outwardly upwardly and being disposed in a triangular configuration, the female portion comprising three conical pins which are partially embedded within a mass of plastics material, said three pins having their axes parallel and being disposed in a triangular configuration, the mass of plastics material having an aperture permitting the pins to be engaged with the frustoconical drillings of the coupling portion of the male portion.

2. A dental attachment as claimed in claim 1, in which the lower end of each of the three pins has a locking lip which co-operates with the lower edge of the coupling member of the male portion.

* * * * *